United States Patent [19]
Meng et al.

[11] Patent Number: 6,083,510
[45] Date of Patent: Jul. 4, 2000

[54] **HIGH MOLECULAR WEIGHT EXTRACTS OF *CONVOLVULUS ARVENSIS* FIELD (FIELD BINDWEED)**

[75] Inventors: Xiaolong Meng; Hugh D. Riordan; Neil H. Riordan, all of Wichita, Kans.

[73] Assignee: The Center for the Improvement of Human Functioning, Int'l., Inc., Wichita, Kans.

[21] Appl. No.: 09/249,874

[22] Filed: Feb. 16, 1999

[51] Int. Cl.$^7$ .................................................. A01N 65/00
[52] U.S. Cl. ........................................................ 424/195.1
[58] Field of Search ........................................... 424/195.1

[56] References Cited

PUBLICATIONS

Computer Derwent Abstract JP007238011 "Safe and Highly Effective Skin–Whitening Cosmetic Material Contains Extracts of Baliospermum Montanum, Melia Azadirachta and Convolvulus Arvensis", Sep. 12, 1995

*Primary Examiner*—Herbert J. Lilling
*Attorney, Agent, or Firm*—Knobbe, Martens, Olson & Bear, LLP

[57] ABSTRACT

A purified bindweed extract is used to inhibit the growth of tumor cells, inhibit the growth of blood vessels, and enhance immune function. The bindweed extract is prepared by removing toxic low molecular weight components of *Convolvulus arvensis*.

24 Claims, No Drawings

HIGH MOLECULAR WEIGHT EXTRACTS OF *CONVOLVULUS ARVENSIS* FIELD (FIELD BINDWEED)

FIELD OF THE INVENTION

This invention relates to obtaining purified bindweed extracts by collecting high molecular weight components of a homogenized aqueous solution of bindweed material. These high molecular weight extracts have unexpectedly been shown to inhibit the growth of two different types of virulent tumors in mice. The extracts possess immunopotentiating effects as evidenced by tumor infiltration by white blood cells in the tumors of treated animals, and induction of lymphocyte proliferation. They further possess antiangiogenic properties as demonstrated in the chick chorioallantoic membrane assay. The method of extraction allows for the removal of small molecules, including alkaloids, from the plant material, which are known to be toxic. The bindweed extracts have utility as low-toxicity, anti-cancer drugs for human and animal use.

BACKGROUND OF THE INVENTION

Recently the concept of using biological response modifiers (BRMs) has been considered for the treatment of cancer. Some BRMs are not directly cytotoxic to tumor cells, but possess qualities which change the environment of the organism. Immune stimulation and inhibition of new blood vessel growth are two biological response modification strategies with potential in the treatment of cancer. Examples of immune stimulators with known anti-tumor activity are Polysaccharide K, beta 1,3, glucan, and the Maruyama vaccine. All of which contain high-molecular weight polysaccharides and/or protein. Examples of angiogenesis inhibiting molecules include TMP-470, and angiostatin, which have demonstrated anti-tumor activity. While investigating extracts of field bindweed for anti-tumor activity, we initially tried to isolate low-molecular weight alkaloids, which are known to be toxic, and which we suspected of having traditional chemotherapeutic, or tumor-cytotoxic activity.

It was found that the low-molecular weight extracts, containing the toxic alkaloids, exhibited little anti-tumor activity, while high molecular weight extracts, which excluded the toxic alkaloids contained significant anti-tumor activity by acting as biological response modifiers.

SUMMARY OF THE INVENTION

One object of the invention is to provide a pharmaceutical consisting of high molecular weight extracts of field bindweed (*Convolvulus arvensis*) which have low toxicity to normal cells and induce anti-tumor effects in animals, inhibit the growth of blood vessels, and enhance immune function in mammals. Preferably these high molecular weight extracts have components less than about 500 Daltons removed. More preferably the removed components are less than about 1,000. Even more preferably, the removed components are less than about 3,000 Daltons. Even more preferably, the removed components are less than about 5000, more preferably 10,000.

One embodiment of the invention is to isolate the high molecular weight extracts of field bindweed (*Convolvulus arvensis*) using a molecular weight filter or alternatively precipitation with ammonium sulfate.

A further object of the present invention is to provide a method for isolating high molecular weight extracts of field bindweed (*Convolvulus arvensis*), which have low toxicity by virtue of removal of toxic low-molecular weight components of a crude extract. Preferably the components less than about 3000 Daltons are removed. More preferably the components less than about 6,500 Daltons are removed. Even more preferably, the components less than about 10,000 Daltons are removed.

One embodiment of the invention is to remove the low molecular weight extracts of field bindweed (*Convolvulus arvensis*) using a molecular weight filter or alternatively precipitation with ammonium sulfate.

A further object of the present invention is to provide a method for use of high molecular weight extracts of field bindweed (*Convolvulus arvensis*), which have low toxicity to normal cells and induce anti-tumor effects in animals.

A further object of the present invention is to provide a method for use of high molecular weight extracts of field bindweed (*Convolvulus arvensis*), which inhibit new blood vessel growth.

A further object of the present invention is to provide a method for use of high molecular weight extracts of field bindweed (*Convolvulus arvensis*), which exhibits immunoenhancing effects in animals.

These and other objects of the invention will become more apparent by reference to the materials and methods hereinafter set forth.

DETAILED DESCRIPTION OF THE PREFERRED EMBODIMENTS

We discovered a high molecular weight extract of bindweed that surprisingly has low toxicity to normal cells and induces anti-tumor effects, inhibits the growth of blood vessels, and enhances immune function in mammals. We also found that the low molecular weight components of bindweed extract contained alkyloids on the order of 300–500 Daltons that were toxic to both normal cells and tumor cells. In order to remove the toxic low molecular weight components we used a molecular weight sieve. In general, the method of the invention for obtaining high molecular weight extracts of *Convolvulus arvensis* consists of boiling fresh or aged bindweed in an aqueous solution to obtain a brown tea-like mixture. This mixture is then centrifuged or filtered to remove the solid material to create a solution. It is only necessary to remove the 300–500 molecular weight components to remove the toxicity to normal cells. However, we found that the low molecular weight components might nonspecifically stick to the membrane and come back off. Therefore, preferably, a larger molecular weight sieve is used—on the order of 1000 Daltons, more preferably, 3000 Daltons, even more preferably 5000 Daltons. We find that even when molecular weight components of up to 10,000 Daltons are removed, the extract retains its anti-tumor effects in animals, its ability to inhibit the growth of blood vessels, and its ability to enhance immune function in mammals. In the Examples below, after boiling the fresh or aged bindweed in an aqueous solution to obtain a brown tea-like mixture, the solution is then passed through a molecular weight filtration device to obtain a high molecular weight retentate (BWR), or precipitated using ammonium sulfate to isolate a high molecular weight precipitate (BWP). Thereafter, the high molecular weight extract is lyophilized, or otherwise concentrated. The extract is subsequently assayed for anti-tumor, immunoenhancing, and anti-angiogenesis activity.

SDS-Page, IEF, and a protein assay, are then used in order to further characterize the components of the extract. The extract is also assayed for molecular weight using a Superose 12-HR sizing column (Pharmacia Biotech) using known molecular weight standards.

Further features and advantages of the present invention will become apparent to those of skill in the art in view of the detailed description of the preferred embodiments which follows when considered together with the attached drawings and claims.

Although other material and methods similar or equivalent to those described herein can be used in the practice or testing of the present invention, the preferred methods and materials are now described. Example 1 describes the steps required to prepare the high molecular weight extracts of bindweed.

EXAMPLE 1

Preparation of High Molecular Weight Extracts of Bindweed

We have isolated high molecular weight extracts of *Convolvulus arvensis* as follows. Fresh *Convolvulus arvensis* was harvested and the seeds, and flowers, were discarded. These portions of the plants were homogenized using a Waring blender. To the homogenized plant material, 3 volumes of deionized water were added to create a mixture. This mixture was then boiled for 30 minutes to obtain a tea. The solids were removed from the tea by filtration, and the supernatant retained. The supernatant was cooled and from it two high molecular weight isolates were prepared. Some of the tea supernatant was processed in a CH2 concentrator equipped with a 3,000 or greater Dalton cartridge. The retentate of the concentrator (containing only molecules larger than 3,000 Daltons) was retained, and lyophilized, and is herein referred to as BWR. Alternatively, some of the tea supernatant was combined with ammonium sulfate to yield a final saturation of 50% ammonium sulfate. This resulted in precipitation of some of the components of the tea supernatant. The precipitated components were then collected after centrifugation at 25,000 g for 30 minutes, and resuspended in phosphate buffered saline to form a new solution. This new solution was then passed through a ultrafiltration device using a 3,000 Dalton membrane. The retentate was collected, and lyophilized, and herein referred to as BWP. BWP, and BWR, were stored at 4° C. in a dessicator prior to use in characterization, and anti-tumor, anti-angiogenesis, and immune parameter studies.

In Examples 2 and 3, the high molecular weight extracts were characterized and tested for toxicity.

EXAMPLE 2

Characterization of High Molecular Weight Extracts of Bindweed

SDS-Page analysis of BWR and BWP both showed a generalized smearing pattern, which is a polysaccharide characteristic, with occasional protein bands at various molecular weights ranging from greater than 200,000 Daltons to 6,500 Daltons. Both extracts were positive for the Molish reaction, which indicates the presence of sugar moieties. And both were strongly positive for protein using the bicinchroninic acid assay. The above leading to the conclusion that BWP, and BWR contain both protein and saccharide. FPLC chromatography of BWR, and BWP using a Superose 12-HR sizing column demonstrate only high molecular weight peaks with no detection of molecules smaller than 10,000 Daltons.

EXAMPLE 3

Characterization of Toxicity of High Molecular Weight Extracts of Bindweed

Standard chemotherapy screening for cytotoxic anti-tumor agents selects for agents with cytotoxic activity at a concentration of 5 mcg/mL. Both extracts of bindweed were only toxic to cultured tumor cells at concentrations of 1000 mcg/mL or greater, demonstrating low toxicity.

In Examples 4 through 10 the effects of the high molecular weight extracts, BWR and BWP were analyzed as to anti-angiogenesis activity, anti-tumor activity and effect on immune function.

EXAMPLE 4

Anti-angiogenesis Activity of BWR

The high molecular weight saccharide/protein containing extracts of bindweed were prepared in accordance with the above-mentioned methods.
The anti-angiogenesis activity of BWR was examined. Angiogenesis was induced on chicken egg chorioallantoic membranes by placing a 2 mm methylcellulose disc containing 10 mcg of heparin onto 11 day old chicken egg chorioallantoic membranes. Doses of 200, 100, and 50 mcg of BWR, were concomitantly added to the heparin-containing disc in three sets of 6 eggs each. 6 eggs served as controls. After 4 days, a large window was created over the chorioallantoic membranes, and the numbers of new blood vessels on each egg were counted.

A percent inhibition on angiogenesis was obtained according to the following equation:

Angiogenesis inhibition (%)=(1−Average number of new blood vessels of test group/Average number of new blood vessels of control group)×100

The results obtained are shown in Table 1 below. It is seen that the angiogenesis, or the induction of new blood vessels was significantly inhibited by the administration of BWR, in a dose-dependent manner.

TABLE 1

| Angiogenesis inhibition | | |
|---|---|---|
| 200 mcg/egg | 100 mcg/egg | 50 mcg/egg |
| 73% | 55% | 18% |

EXAMPLE 5

Antitumor Activity of BWR

The antitumor effects of BWR, prepared as described above, were examined. Ten 6-week-old mixed-gender Kun Ming mice per group were used as test animals. S-180 fibrosarcoma cells were subcutaneously transplanted to the left inguinal region. Daily for 14 days, BWR was injected subcutaneously in the right inguinal region. On the 15th day after the transplantation, the tumor was excised and weighed. A percent inhibition on tumor growth was obtained according to the following equation:

Tumor growth inhibition (%)=(1−Average tumor weight of test group/Average tumor weight of control group)×100

The results obtained are shown in Table 2 below. It is seen that tumor growth was significantly inhibited by the administration of BWR.

TABLE 2

| Group | Dose Dose In mg | Average Tumor Weight | Tumor Growth Inhibition (%) |
|---|---|---|---|
| Control | 0 | 1.4 | |
| BWR | 1 × 14 | 0.32 | 77 |

EXAMPLE 6

Antitumor Effects of BWP

Additionally, the antitumor effects of BWP were examined. Ten 6-week-old mixed-gender Kun Ming mice per group were used as test animals. S-180 cells were subcutaneously transplanted to the left inguinal region. Daily for 14 days, BWP was injected subcutaneously in the right inguinal region. On the 15th day after the transplantation, the tumor was excised and weighed. A percent inhibition on tumor growth was obtained according to the following equation:

Tumor growth inhibition (%)=(1−Average tumor weight group/Average tumor weight control group)×100

The results obtained are shown in Table 3 below. It is seen that tumor growth was significantly inhibited by the administration of BWP.

TABLE 3

| Group | Dose Dose In mg | Average Tumor Weight | Tumor Growth Inhibition (%) |
|---|---|---|---|
| Control | 0 | 2.5 | |
| BWP | 1 × 14 | 0.6 | 74 |

EXAMPLE 7

Further Antitumor Effects of BWP

The antitumor effects of BWP were examined further. Ten 6-week-old C57 mixed-gender mice per group were used as test animals. LLC, Lewis Lung Carcinoma Cells were subcutaneously transplanted to the left inguinal region. Daily for 21 days, BWR was injected subcutaneously in the right inguinal region. On the $22^{nd}$ day after the transplantation, the tumor was excised and weighed. A percent inhibition on tumor growth was obtained according to the following equation:

Tumor growth inhibition (%)=(1−Average tumor weight group/Average tumor weight control group)×100

The results obtained are shown in Table 4 below. It is seen that tumor growth was significantly inhibited by the administration of BWP.

TABLE 4

| Group | Dose Dose In mg | Average Tumor Weight | Tumor Growth Inhibition (%) |
|---|---|---|---|
| Control | 0 | 3.5 | |
| BWP | 1 × 21 | 1.33 | 62 |

EXAMPLE 8

Further Antitumor Effects of BWR

The antitumor effects of BWR were examined further. Ten 6-week-old mixed-gender Kun Ming mice per group were used as test animals. S-180 cells were subcutaneously transplanted to the left inguinal region. Daily for 14 days, BWP was injected intraperitoneally. On the $15^{th}$ day after the transplantation, the tumor was excised and weighed. A percent inhibition on tumor growth was obtained according to the following equation:

Tumor growth inhibition (%)=(1−Average tumor weight group/Average tumor weight control group)×100

The results obtained are shown in Table 5 below. It is seen that tumor growth was significantly inhibited by the administration of BWR.

TABLE 5

| Group | Dose Dose In mg | Average Tumor Weight | Tumor Growth Inhibition (%) |
|---|---|---|---|
| Control | 0 | 2.5 | |
| BWR | 1 × 14 | 0.8 | 68 |

The tumors from this study were embedded in paraffin, stained, and examined microscopically. It was found that the excised tumors from the treated group contained large numbers of lymphocytes and monocytes, and only 10% tumor tissue. The weight of tumor tissue from the tumor tissue in the treated groups was therefore only 10% of that recorded, or 0.08 grams rather than 0.8 grams. Therefore the actual inhibition was 96.8%. These results also demonstrate that BWR contains a quality which enhances the immune response to tumor tissue.

EXAMPLE 9

Effects of BWR and BWP on Human Lymphocyte Growth

The effects of BWR, and BWP on human lymphocyte growth in culture were examined. Human lymphocytes were harvested using venipuncture, and subsequently isolated by use of a centrifuged density gradient. They were then incubated in a commercial lymphocyte culture medium (AIM V, containing interleukin 2 and 2 mercaptoethanol) in an atmosphere containing 95% air, 5% carbon dioxide, at 37° C., for 3 days. The lymphocytes were then counted using a Coulter Epics XL flow cytometer. A percent increase in lymphocyte growth was obtained according to the following equation:

Lymphocyte growth increase (%)=(Average number of lymphocytes of test group/Average number of lymphocytes of control group×100)−100

The results obtained are shown in Table 6 below. It is seen that BWR, and BWP induced lymphocyte proliferation, in a dose-dependent manner.

TABLE 6

| Dose (mcg/ml) | 0 | .8 | 4 | 20 | 100 |
|---|---|---|---|---|---|
| BWR | 0 | 0 | 20 | 0 | 35 |
| BWP | 0 | 12 | 35 | 20 | 46 |

EXAMPLE 10

Effects of BWR and BWP on Human Phagocytic Activity

The effects of BWR, and BWP on human phagocyte activity were examined. Two buffy-coat samples were prepared by centrifuging tubes containing anti-coagulated human blood from two subjects. The samples were then divided in two. To one buffy-coat from each subject, 2 micrograms of BWR, and BWP were added. One buffy-coat from each subject served as control. All samples were incubated for 5 hours. Then 30 milligrams of freshly rehydrated baker's yeast was added to all samples. After one hour, a stock 2× solution of acridine orange stain was added to each sample. An aliquot of each sample was then placed on a microscope slide. The percentage of phagocytes containing intracellular baker's yeast from each sample was recorded.

The results revealed an average increase of 85% in the percentage of phagocytes containing intracellular baker's yeast in the treated samples compared to the controls. This elucidates another mechanism by which BWR and BWP stimulate the immune system.

What is claimed is:

1. A pharmaceutical composition for treating cancer, inhibiting the growth of new blood vessels, and/or enhancing immune function in a mammal, said composition comprising: an effective amount of an aqueous extract of *Convolvulus arvensis* prepared by a process comprising:

homogenizing *Convolvulus arvensis* plant parts;

preparing said aqueous extract from said plant parts; and substantially removing components from said extract of molecular weight less than about 500 Daltons, said pharmaceutical composition further comprising a pharmaceutically acceptable vehicle.

2. The pharmaceutical composition of claim 1 wherein components of molecular weight less than about 1000 Daltons have been removed.

3. The pharmaceutical composition of claim 2 wherein components of molecular weight less than about 3000 Daltons have been removed.

4. The pharmaceutical composition of claim 3 wherein components of molecular weight less than about 5000 Daltons have been removed.

5. The pharmaceutical composition of claim 4 wherein components of molecular weight less than about 10,000 Daltons have been removed.

6. A method for preparing non-toxic extracts of Convolvulus arvensis consisting of; removing components with a molecular weight less than about 500 Daltons.

7. The method of claim 6 wherein components with a molecular weight less than about 1000 Daltons are removed.

8. The method of claim 7 wherein components with a molecular weight less than about 3000 Daltons are removed.

9. The method of claim 8 wherein components with a molecular weight less than about 5000 Daltons are removed.

10. The method of claim 9 wherein components with a molecular weight less than about 10,000 Daltons are removed.

11. The method of claim 6 wherein said components are removed using a molecular weight filter.

12. The method of claim 6 wherein said components are removed by precipitation with ammonium sulfate.

13. A method for the treatment of cancer in a mammal comprising the steps of:

administering the pharmaceutical composition of claim 1 in an amount effective to slow or stop the growth of said cancer.

14. A method for inhibiting blood vessel growth in a mammal comprising the steps of:

administering the pharmaceutical composition of claim 1 in an amount effective to slow or stop the growth of said blood vessels.

15. A method for enhancing immune function in a mammal comprising the steps of:

administering the pharmaceutical composition of claim 1 in an amount effective to enhance said immune function.

16. The method of claim 15 wherein the immune function is selected from the group consisting of lymphocyte growth and phagocyte activity.

17. The composition of claim 1, wherein the plant parts exclude seeds and flowers.

18. The composition of claim 1, wherein the extract is prepared using three volumes of water per volume of homogenized plant parts.

19. The composition of claim 1, wherein solids are removed from the extract.

20. The composition of claim 1, wherein the extract is lyophilized after removal of said components.

21. The composition of claim 1, wherein the extract is subjected to ammonium sulfate precipitation.

22. The composition of claim 21, wherein the extract subjected to precipitation is centrifuged to collect the precipitates.

23. The composition of claim 22, wherein the precipitates are resuspended in phosphate buffer.

24. The composition of claim 23, wherein the resuspended precipitates are subjected to ultrafiltration to remove said components.

* * * * *